US012721797B2

(12) United States Patent
Zhang et al.

(10) Patent No.: US 12,721,797 B2
(45) Date of Patent: Sep. 1, 2026

(54) COMPOSITION FOR CARING FOR KERATIN MATERIALS AND USE THEREOF

(71) Applicant: L'OREAL, Paris (FR)

(72) Inventors: Shichen Zhang, Shanghai (CN); Cherry Yang, Shanghai (CN); Jessica Yuan, Shanghai (CN)

(73) Assignee: L'OREAL, Paris (FR)

( * ) Notice: Subject to any disclaimer, the term of this patent is extended or adjusted under 35 U.S.C. 154(b) by 696 days.

(21) Appl. No.: 17/790,004

(22) PCT Filed: Dec. 31, 2019

(86) PCT No.: PCT/CN2019/130373
§ 371 (c)(1),
(2) Date: Jun. 29, 2022

(87) PCT Pub. No.: WO2021/134420
PCT Pub. Date: Jul. 8, 2021

(65) Prior Publication Data
US 2023/0047565 A1 Feb. 16, 2023

(51) Int. Cl.
*A61K 8/37* (2006.01)
*A61K 8/36* (2006.01)
*A61K 31/20* (2006.01)
*A61K 31/23* (2006.01)
*A61P 17/04* (2006.01)
*A61Q 5/12* (2006.01)

(52) U.S. Cl.
CPC .............. *A61K 8/375* (2013.01); *A61K 8/361* (2013.01); *A61K 31/20* (2013.01); *A61K 31/23* (2013.01); *A61P 17/04* (2018.01); *A61Q 5/12* (2013.01)

(58) Field of Classification Search
None
See application file for complete search history.

(56) References Cited

U.S. PATENT DOCUMENTS 9,821,040 B2 11/2017 Richon
10,568,944 B2 2/2020 Richon
2005/0058673 A1* 3/2005 Scholz ................ A61K 9/0046 514/557
2010/0016430 A1 1/2010 Long
2015/0238576 A1 8/2015 Richon
2018/0036390 A1 2/2018 Richon
2018/0036391 A1 2/2018 Richon
2018/0036392 A1 2/2018 Richon

FOREIGN PATENT DOCUMENTS

CN 106389284 A 2/2017
DE 44 35 290 A1 4/1996
WO WO 2007/067028 A1 6/2007

OTHER PUBLICATIONS

International Search Report issued Sep. 27, 2020, in PCT/CN2019/130373, 4 pages.
Meng, Pengcheng. "Lipase-catalyed Transesterification of Coconut Oil for Meduim Carbon Chain Triacylglycerols", Master dissertation, Henan University of Technology, Dec. 31, 2015, 87 pages.
Extended European Search Report issued Sep. 13, 2023 in European Patent Application No. 19958109.1, 10 pages.
Haris, H. et al., "Evaluation of Efficacy and Safety of *Avco Acne Gel* for Acne: An Open, Single Centric, Non Comparative Study for 8 Weeks," Asian Journal of Pharmaceutical and Clinical Research, vol. 5, No. Suppl 3, 2012, XP093078583, pp. 73-76.
Haron U., et al., "The Comparative Antimicrobial Effect of Activated Virgin Coconut Oil (AVCO) and Virgin Coconut Oil (VCO) against Dental Caries-Related Pathogens," Advances in Health Science Research, vol. 8, 2017, XP93078705, pp. 312-317.
Haron U., et al., "Fatty Acid Evaluation and Antimicrobial Activity of Virgin Coconut Oil and Activated Virgin Coconut Oil on *Streptococcus mutans*," Archives of Orofacial Sciences, vol. 14, Issue 2, 2019, XP93078711, pp. 87-98.
"Mosquito Repellent," Database GNPD [Online] Mintel, Dec. 20, 2019, XP93078726, 4 pages.

* cited by examiner

*Primary Examiner* — David J Blanchard
*Assistant Examiner* — Kaeleigh E Olsen
(74) *Attorney, Agent, or Firm* — Oblon, McClelland, Maier & Neustadt, L.L.P.

(57) ABSTRACT

A composition for caring for keratin materials, comprising a fatty acid-ester mixture of a plurality, e.g., at least 3, 4, or 5, of medium chain fatty acids and a plurality, e.g., at least 3, 4, or 5, of monoesters; and a cosmetically or dermatologically acceptable auxiliary agent to assist the delivery of the fatty acid-ester mixture to the keratin materials.

9 Claims, 1 Drawing Sheet

COMPOSITION FOR CARING FOR KERATIN MATERIALS AND USE THEREOF

TECHNICAL FIELD

Figure 1:
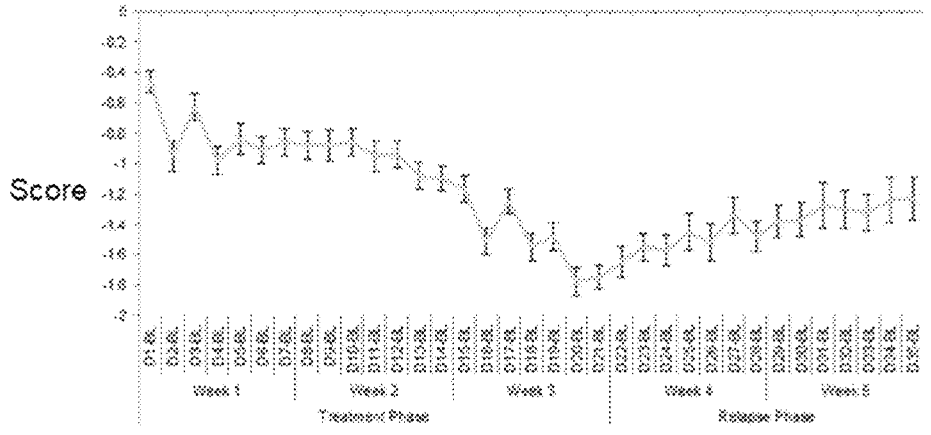

The present invention relates to a composition for caring for keratin materials, in particular the scalp. The invention also relates to a process for caring for keratin materials, in particular the skin, scalp and/or hair, using the composition of the present invention.

BACKGROUND

Keratin materials are present widely on surface of human bodies, e.g., skin, scalp and hair. Many people have for a long time sought to soothing the body surface, so as to feel comfortable in daily life and work. Amongst others, the feeling of itch is particularly concerned by many people. Various factors may cause the feeling of itch, e.g., high dryness of body surface, presence of certain bacteria on body surface, allergy, external stimuli (e.g., wind blowing, friction, climate, humidity, or pollution), inflammation of skin, or even psychological feeling, etc. Accordingly, various products are developed to deal with the itchy feeling of person, many of which are used to soothe the feeling of itch. In particular, considering the various factors, soothing the feeling of itchy is usually more feasible and meaningful than therapeutic treatment against directly the factors.

In the keratin materials on body surface, the scalp is particularly readily to suffer from itch. Various formulations have been developed for the itchy scalp, including those provided in a separate form, e.g., lotion, spray and the like, and those incorporated into conventional products for hair and/or for scalp, e.g., shampoo, leave-on and/or rinse-off conditioner.

On the other hand, for cosmetic uses, natural ingredients, i.e., ingredients of natural origin, are of great interest to the consumers. Many compounds with natural origin are used in formulating compositions for caring for and/or making up of keratin materials. Efforts have been made to formulate compositions comprising natural ingredients.

SUMMARY OF THE INVENTION

In medical science, medium chain fatty acids and the respectively corresponding monoglycerides have been disclosed to have a broad spectrum of anti-microbial activity against enveloped viruses and various bacteria in vitro (Kabara, 1978; Shibasaki and Kato, 1978; Welsh et al. 1979 Thormar et al., 1987; Isaacs et al. 1995), comprising but not limited to human pathogens such as herpes simplex virus, *Candida albicans, Chlamydia trachomatis, Neisseria gonorrhoeae, Helicobacter pylori* and *Staphylococcus aureus*. The inventors have now discovered that the use of a fatty acid-ester mixture of a plurality, e.g., at least 3, 4, or 5, of medium chain fatty acids and monoesters of the respective medium chain fatty acids with a lower polyol, makes it possible to obtain a composition for caring for keratin materials, which can non-therapeutically soothe the itchy feeling occurring on the keratin materials, especially on scalp.

One subject of the present invention is thus a non-therapeutically anti-itching composition for caring for keratin materials comprising:

- a fatty acid-ester mixture of a plurality, e.g., at least 3, 4, or 5, of medium chain fatty acids and a plurality, e.g., at least 3, 4, or 5, of monoesters; and
- a cosmetically or dermatologically acceptable auxiliary agent to assist the delivery of the fatty acid-ester mixture to the keratin materials.

According to an embodiment of the invention, the fatty acid-ester mixture is a derivative of coconut oil, called as activated virgin coco oil (AVCO).

The present invention also relates to a process for soothing the feeling of itching of keratin materials, in particular keratin materials on body surface, especially scalp, using the anti-itching composition according to the invention.

The present invention thus provides use of the fatty acid-ester mixture for soothing the feeling of itching of keratin materials on body surface, especially scalp.

Notably, as introduced above, although medium chain fatty acids and monoglycerides thereof are known to have anti-microbial activity, various factors may cause the feeling of itch. The composition of the invention has been discovered, and also has been proved through experiments, that itchy feeling can be successfully soothed. Without being restricted to any known theory, it is believed that the successful use of the composition of the invention to soothe the itchy feeling contributes at least a part to the sensory relax to the keratin materials by the composition of the invention. Accordingly, the composition of the invention is limited to non-therapeutic uses, though it may be discovered further properties and/or mechanisms for a therapeutic use in the future.

EMBODIMENTS OF THE INVENTION

Throughout the description, including the claims, the term "comprising a" should be understood as being synonymous with "comprising at least one", unless otherwise mentioned. Moreover, the expression "at least one" used in the present description is equivalent to the expression "one or more".

Throughout the description, including the claims, an embodiment defined with "comprising" or the like should be understood to encompass a preferable embodiment defined with "consisting substantially of" and a preferable embodiment defined with "consisting of".

Other than in the operating examples, or where otherwise indicated, all numbers expressing quantities of components and/or reaction conditions are to be understood as being modified in all instances by the term "about," meaning within 10% of the indicated number (e.g. "about 10%" means 9%-11% and "about 2%" means 1.8%-2.2%).

Throughout the description, including the claims, the "keratin material" according to the present invention is the skin, hair, scalp, eyelashes, eyebrows, bodily hair, nails, lips or mucous membranes. Preferably, the keratin material according to the present invention is a position where an itchy feeling is easily felt, e.g., scalp, or skin, and/or a position where the itchy feeling has an impact on, e.g., hair.

Throughout the description, including the claims, the "care for", "caring for" and the like according to the present invention should be understood to encompass any means to take care, maintain or improve the status of keratin materials, including not only the conventional means of caring for keratin materials, e.g., skin or scalp, but also any means known to be useful for conditioning and/or cleansing keratin materials, e.g., hair or scalp.

In the application, unless specifically mentioned otherwise, contents, parts and percentages are expressed on a weight basis.

The present invention is directed to a non-therapeutic composition for caring for keratin materials, comprising:

(A) a fatty acid-ester mixture comprising:

(A-I). a fatty acid component comprising a plurality, e.g., at least 3, 4, or 5, of medium chain fatty acids, and (A-II). an ester component comprising a plurality, e.g., at least 3, 4, or 5, of monoesters of medium chain fatty acids; and (B) a cosmetically or dermatologically acceptable auxiliary agent to assist the delivery of the fatty acid-ester mixture (A) to the keratin materials.

Preferably, the monoesters of the ester component (A-II) are respectively obtained from esterification of the medium chain fatty acids used in component (A-I) with a lower polyol.

Preferably, the fatty acid-ester mixture is a derivative of coconut oil, called as activated virgin coco oil (AVCO).

The present invention thus provides use of the composition of the present invention for soothing the feeling of itching of keratin materials on body surface, especially scalp, wherein the composition comprises fatty acid-ester mixture.

Advantageously, the present invention provides use of fatty acid-ester mixture for soothing the feeling of itching of keratin materials on body surface.

The present invention also relates to a process for soothing the feeling of itching of keratin materials, in particular keratin materials on body surface, especially scalp, using the anti-itching composition according to the invention.

Other characteristics and advantages of the invention will emerge more clearly on reading the description and the examples that follow.

Fatty acid-ester Mixture (A)

The composition of the present invention comprises a fatty acid-ester mixture (A) of a plurality, e.g., at least 3, 4, or 5, of medium chain fatty acids and monoesters of the respective medium chain fatty acids with a lower polyol.

The useful fatty acid component (A-I) according to the present invention is a medium chain fatty acid, e.g., preferably a monocarboxylic acid having 6 to 20 carbon atoms, preferably 8-16 carbon atoms, more preferably 8-12 carbon atoms. Accordingly, the fatty acid can have a formula (I):

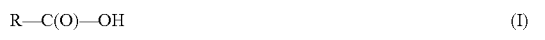

R—C(O)—OH (I)

wherein:

R represents a linear or branched, saturated or unsaturated $C_5$-$C_{19}$, preferably $C_7$-$C_{15}$, more preferably $C_7$-$C_{11}$, hydrocarbyl group, preferably alkyl; and preferably, R is a linear group; and more preferably, R is a linear alkyl.

According to an embodiment of the present invention, R has preferably has an odd number, e.g., 5, 7, 9, 11, 13, 15, 17 or 19, of carbon atoms. More preferably, R has 7, 9, 11, 13 or 15 carbon atoms; or preferably, R has 7, 9 or 11 carbon atoms.

According to an embodiment of the present invention, the medium chain fatty acid can be used alone or as a combination of two or more fatty acids. Preferably, the medium chain fatty acid is used as a combination of at least 3, 4, or 5 fatty acids.

The useful fatty acid according to the present invention can be preferably at least partially esterified with a polyol.

According to an embodiment of the present invention, the monoester useful as component (A-II) is a monoester of formula (II):

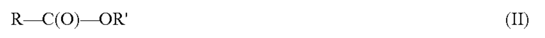

R—C(O)—OR' (II)

wherein:

R is as defined in formula (I).

R' represents a residue from a polyol. The useful polyol especially contains from 2 to 20 carbon atoms, preferably containing from 2 to 10 carbon atoms and preferably containing from 2 to 6 carbon atoms, such as glycerol, propylene glycol, butylene glycol, pentylene glycol, hexylene glycol, dipropylene glycol or diethylene glycol.

Preferably, the fatty acid according to formula (I) includes caprylic acid (C8, also called as octoic acid), capric acid (C10), lauric acid (C12), myristic acid (C14), palmitic acid (C16), stearic acid (C18), or arachidic acid (C20).

More preferably, in the formula (II), R and R' are different from one another, wherein R represents a linear $C_7$-$C_{15}$ alkyl, and R' represents a residue from a linear polyol containing from 2 to 6 carbon atoms.

According to an embodiment of the present invention, the fatty acid according to formula (I) is preferably used in combination with the monoester according to formula (II), so as to form the fatty acid-ester mixture (A). Preferably, the fatty acid and the monoester for the mixture (A) involve the same fatty acid moiety, i.e., the fatty acid of formula (I) and the monoester of formula (II) having the corresponding R group. That is, if a fatty acid of formula (I) having octyl as R, i.e., being a caprylic acid, is used, then, a monoester of formula (II) having octyl as R, i.e., being a monoester of caprylic acid, is used, to form the fatty acid-ester mixture (A). Also, if two or more fatty acids are concurrently used for the mixture (A), then the corresponding two or more monoesters respectively having the same fatty acid moieties are used. In other words, according to an embodiment of the present invention, the fatty acid-ester mixture (A) can be deemed as a mixture of two or more fatty acids of formula (I) and the partially esterified monoesters of the each fatty acid.

According to an embodiment of the present invention, the fatty acid-ester mixture (A) comprises a plurality, e.g., at least 3, 4, or 5, of fatty acids of formula (I) and monoesters of formula (II) having the corresponding R groups respectively same as the fatty acids of formula (I). Corresponding to the fatty acid moieties, it is preferred that a same polyol is used to form the monoesters. That is, for the two more monoesters of formula (II) for the fatty acid-ester mixture (A), they have the same R' group. Amongst others, glycerol is particularly used, so as to form glycerides with the variously corresponding fatty acids mentioned above.

According to an embodiment of the present invention, for example, the fatty acid-ester mixture (A) comprises at least 3 fatty acids selected from the group consisting of caprylic acid, capric acid, lauric acid, myristic acid, palmitic acid, stearic acid, and arachidic acid, to be used as component (A-I). Meanwhile, the corresponding monoesters of the each fatty acid in component (A-I) are used as component (A-II). Preferably, the monoesters of component (A-II) is each a glyceride.

Preferably, according to an embodiment of the present invention, the fatty acid component (A-I) comprises caprylic acid, capric acid, and lauric acid. Meanwhile, the corresponding component (A-II) comprises caprylic glyceride (also called as monocaprylin), capric glyceride (also called as monocaprin), and lauric glyceride (also called as monolaurin).

According to an embodiment of the present invention, for example, regarding the fatty acid-ester mixture (A), the total amount of fatty acids of component (A-I) and the total amount of monoesters of component (A-II), e.g., glycerides, thereof are present in a ratio ranging from 4:1 to 1:1, preferably 3:1 to 1:1, more preferably 2.5:1 to 1.5:1.

According to an embodiment of the present invention, for example, the fatty acid-ester mixture (A) can be obtained by partially esterifying directly the fatty acid component (A-I) with a polyol to form monoesters, so as to obtain a mixture of fatty acids and the corresponding monoesters as ester component (A-II). As a polyol is used, it is well understood that a multiester, e.g., diester, triester and the like, may be finally formed. Accordingly, a fatty acid-ester mixture (A) comprising at least 3 fatty acids, monoesters corresponding to the at least 3 fatty acids, and multiesters corresponding to the at least 3 medium chain fatty acids, is still useful for the purpose of the present invention, as long as the main purpose, in particular the anti-itching effect, is not significantly damaged.

For the purpose of the present invention, term "multiester" is provided to mean an ester formed from an esterification of a polyol, wherein more than one hydroxyl group of a polyol molecule is esterified. Accordingly, "diester" and "triester" according to the present invention mean respectively two and three hydroxyl groups of a polyol molecule is esterified.

For example, when glycerol is used to esterify a fatty acid component (A-I), the useful fatty acid-ester mixture (A) may comprise at least 3 fatty acids, monoesters, diesters and triesters corresponding to the at least 3 fatty acids. For example, the useful fatty acid-ester mixture (A) may comprise caprylic acid, capric acid, and lauric acid, as component (A-I); monocaprylin, monocaprin, and monolaurin, as component (A-II); and diglyceride and triglyceride of caprylic acid, capric acid, and lauric acid.

When the fatty acid-ester mixture (A) also comprises a multiester, the content of the multiester is not particularly limited, as long as the main purpose, in particular the anti-itching effect, of the mixture (A) is not significantly damaged. For example, the multiester can be used in the mixture (A) in an amount up to 90 wt %, preferably 80 wt % or less, or preferably 70 wt % or less, or preferably 65 wt % or less.

AVCO

According to an embodiment of the present invention, for example, the fatty acid-ester mixture (A) can be of natural origin. Amongst others, it is known that coconut oil comprises a mixture of various C8-C20 fatty acids, especially those having even number of carbon atoms. Thus, it is desirable for the present invention to use a derivative of coconut oil, e.g., an esterified product of coconut oil, as the fatty acid-ester mixture (A).

Amongst others, a useful derivative of coconut oil is the one called as activated virgin coco oil (AVCO). Preferably, the coconut oil is esterified with glycerol. An AVCO useful according to the present invention may comprise caprylic acid, capric acid, and lauric acid, as component (A-I); monocaprylin, monocaprin, and monolaurin, as component (A-II).

According to an embodiment of the present invention, for example, as a useful AVCO, the total amount of fatty acids of component (A-I) and the total amount of mono-glycerides of component (A-II), are present in a ratio ranging from 4:1 to 1:1, preferably 3:1 to 1:1, more preferably 2.5:1 to 1.5:1. More specifically, for example, in exemplary embodiment 1 for AVCO, a useful AVCO may comprise: fatty acid component (A-I): caprylic acid in an amount of 5-20 wt %, preferably 7-15 wt %, or preferably 8-10 wt %; capric acid in an amount of 1-10 wt %, preferably 2-8 wt %, or preferably 4-7 wt %; and lauric acid in an amount of 20-70 wt %, preferably 30-60 wt %, or preferably 40-55 wt %; and monoester component (A-II): monocaprylin in an amount of 0.5-15 wt %, preferably 1-10 wt %, or preferably 4-7 wt %; monocaprin in an amount of 0.1-10 wt %, preferably 1-8 wt %, or preferably 3-5 wt %; and monolaurin in an amount of 10-40 wt %, preferably 15-35 wt %, or preferably 20-30 wt %; each relative to the total amount of the fatty acid component (A-I) and the monoester component (A-II).

An AVCO obtained from the esterification of coconut oil can further comprise diglyceride and triglyceride in addition to the fatty acid component (A-I) and the monoester component (A-II) above. According to an embodiment of the present invention, for example, a useful AVCO may comprise caprylic acid, capric acid, and lauric acid, as component (A-I); monocaprylin, monocaprin, and monolaurin, as component (A-II); and optionally diglyceride and triglyceride of caprylic acid, capric acid, and lauric acid.

When the AVCO also comprises a multiester selected from diglyceride and triglyceride, the content of the multiester is not particularly limited, e.g., in an amount up to 90 wt %, preferably 80 wt % or less, or preferably 70 wt % or less, or preferably 65 wt % or less.

According to an embodiment of the present invention, for example, a useful AVCO may comprise: a fatty acid component (A-I) comprising caprylic acid, capric acid, and lauric acid, in an amount of 5-40 wt %, preferably 10-30 wt %, or preferably 20-25 wt %; a monoester component (A-II) comprising monocaprylin, monocaprin, and monolaurin, in an amount of 1-30 wt %, preferably 5-20 wt %, or preferably 10-15 wt %; diglycerides of caprylic acid, capric acid, and lauric acid, in a sum amount of 10-50 wt %, preferably 20-45 wt %, or preferably 30-40 wt %; and triglycerides of caprylic acid, capric acid, and lauric acid, in a sum amount of 10-70 wt %, preferably 15-50 wt %, or preferably 20-30 wt %; each relative to the total amount of the AVCO.

A useful AVCO can be preferably one prepared according to the teaching by EP 1973415, which disclosure is incorporated herein by reference. Accordingly, an exemplary AVCO can comprise: 24.63 mg/g caprylic acid (C8), 17.81 mg/g capric acid (C10), 133.70 mg/g lauric acid (C12) and 11.82 mg/g monocaprylin, 8.29 mg/g monocaprin and 57.16 mg/g monolaurin; or 23.10 mg/g caprylic acid (C8), 16.08 mg/g capric acid (C10), 116.81 mg/g lauric acid (C12) and 16.04 mg/g monocaprylin, 10.35 mg/g monocaprin and 75.54 mg/g monolaurin; each relative to the total weight of the AVCO; and preferably, the AVCO is derived from catalyzing coconut oil with 1,3-specific lipase and subjecting it to glycerolysis.

The fatty acid-ester mixture (A) may be present in the composition according to the present invention in an amount ranging from 0.01% to 10% by weight, preferably ranging from 0.1% to 5% by weight, or preferably ranging from 0.3% to 1.5% by weight, relative to the total weight of the composition.

Auxiliary Agent (B)

The composition of the present invention comprises at least auxiliary agent (B) to assist the delivery of the fatty acid-ester mixture to the keratin materials.

Amongst others, a solvent is generally used in the auxiliary agent (B).

Solvent

The composition according to the invention can advantageously comprise one or more solvent(s) in the auxiliary agent (B), e.g., water and/or organic solvent.

Water

The composition according to the invention may advantageously comprises water in various amounts. For low viscosity applications of the composition, e.g., in form of lotion, leave-on conditioner, shampoo and the like, a relatively high amount of water may be used. For example, water is used in a content of greater than or equal to 40% by weight relative to the total weight of composition. The water content in the low viscosity composition according to the invention preferably ranges from 40% to 99% by weight, more preferably from 50% to 90% by weight, or from 60% to 80% by weight, relative to the total weight of the composition.

For high viscosity applications of the composition, e.g., in form of cream, rinse-off conditioner, emulsion/microemulsion and the like, a relatively lower amount of water may be used. The high viscosity composition according to the invention advantageously comprises water in a content of less than or equal to 40% by weight relative to the total weight of composition (I). The water content in the low viscosity composition according to the invention preferably ranges from 10% to 40% by weight, more preferably from 15% to 35% by weight, or from 20% to 30% by weight, relative to the total weight of the composition.

Organic Solvent

The composition according to the invention may also comprise one or more organic solvents, preferably water-soluble organic solvents (solubility of greater than or equal to 5% in water at 25° C. and at atmospheric pressure).

Examples of the organic solvents that may be mentioned include linear or branched, and preferably saturated, monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as phenylethyl alcohol; polyols containing more than two hydroxyl functions, such as glycerol; polyol ethers, for instance ethylene glycol monomethyl, monoethyl and monobutyl ether, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

It is known in the art that one category of products can be called as "rinse-off" products, which are applied to users, especially body surface thereof, such as keratin materials thereof, and are subsequently washed off or rinsed off, for example within 1 hour after application. As compared, another category of products can be called as "leave-on" products, which are applied to users, especially body surface thereof, such as keratin materials thereof, without being subsequently washed off or rinsed off. Generally, for a leave-on product, at least one organic solvent, e.g., an alcohol above, can be incorporated.

The organic solvents, when they are present, generally represent between 1% and 20% by weight relative to the total weight of the composition according to the invention, and preferably between 2% and 15% by weight, or between 3% and 8% by weight.

Additional components which are conventionally used in caring for the keratin materials to provide various benefits may be included. The additional components may be selected from surfactant, additional oils, and other additives.

Regarding the surfactant, nonionic, cationic, an anionic, amphoteric surfactant, or a mixture thereof conventionally useful for caring for keratin materials can be used according to the present invention. Amongst others, according to an embodiment of the invention, a cationic surfactant can be preferably used, especially for caring for hairs and the like.

Nonionic Surfactant

According to an embodiment of the invention, the auxiliary component (B) may comprise at least one nonionic surfactant.

Among the useful nonionic surfactants according to the invention, mention may be made, alone or as mixtures, of fatty alcohols, α-diols and alkylphenols, these three types of compound being oxyalkylated such as polyethoxylated and/or polypropoxylated and/or polyglycerolated and containing a fatty chain comprising, for example, 6 to 40 carbon atoms, the number of alkylene oxide such as ethylene oxide or propylene oxide groups possibly ranging especially from 2 to 50 and/or the number of glycerol groups possibly ranging especially from 2 to 30. Mention may also be made of copolymers of ethylene oxide and propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4 glycerol groups, ethoxylated fatty acid esters of sorbitan containing from 2 to 30 mol of ethylene oxide, fatty acid esters of sucrose, fatty acid esters of polyethylene glycol, alkylpolyglycosides, N-alkylglucamine derivatives, amine oxides such as (C10-C14)alkylamine oxides or N-acylaminopropylmorpholine oxides.

Preferably the nonionic surfactant is chosen from:

(poly)ethoxylated fatty alcohols;

glycerolated fatty alcohols;

alkylpolyglycosides.

wherein "fatty chain" means a linear or branched, saturated or unsaturated hydrocarbon-based chain comprising from 6 to 30 carbon atoms and preferably from 8 to 30 carbon atoms.

As regards the alkyl polyglycosides or APGs, these compounds are well known to a person skilled in the art.

These compounds are represented more particularly by the following general formula:

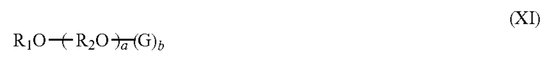

(XI)

in which formula (XI):

$R_1$ represents a saturated or unsaturated, and linear or branched alkyl and/or alkenyl radical comprising from 8 to 24 carbon atoms or an alkylphenyl radical, wherein the linear or branched alkyl radical of which comprises from 8 to 24 carbon atoms;

$R_2$ represents an alkylene radical comprising approximately from 2 to 4 carbon atoms;

G represents a sugar unit comprising from 5 to 6 carbon atoms;

a denotes a value ranging from 0 to 10 and preferably from 0 to 4, and b denotes a value ranging from 1 to 15.

Preferred alkyl polyglycosides useful in the composition of the present invention are compounds of formula (XI) in which $R_1$ more particularly denotes a saturated or unsaturated and linear or branched alkyl radical comprising from 8 to 18 carbon atoms, a denotes a value ranging from 0 to 3 and more particularly still equal to 0, and G can denote glucose, fructose or galactose, preferably glucose.

The degree of polymerization, i.e. the value of b in the formula (I), can range from 1 to 15 and preferably from 1 to 4. The average degree of polymerization is more particularly between 1 and 2 and even more preferably from 1.1 to 1.5.

The glycoside bonds between the sugar units are of 1-6 or 1-4 type and preferably of 1-4 type.

Compounds of formula (XI) are represented in particular by the products sold by Cognis under the names Plantaren® (600 CS/U, 1200 and 2000) or Plantacare® (818, 1200 and 2000). Use may also be made of the caprylyl/capryl glucoside products sold by Seppic under the names Triton CG 110 (or Oramix CG 110) and Triton CG 312 (or Oramix® NS 10), the products sold by BASF under the name Lutensol GD 70 or the products sold by Chem Y under the name AG10 LK.

Use may also be made, for example, of $C_8$-$C_{16}$ alkyl 1,4-polyglucoside as a 53% aqueous solution, sold by Cognis under the reference Plantacare® 818 UP.

As regards the mono- or polyglycerolated surfactants, they preferably comprise on average from 1 to 30 glycerol groups, more particularly from 1 to 10 glycerol groups and in particular from 1.5 to 5.

The monoglycerolated or polyglycerolated surfactants are preferably chosen from the compounds of the following formulae:

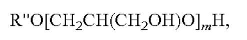

$R''O[CH_2CH(CH_2OH)O]_mH$,

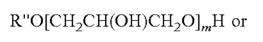

$R''O[CH_2CH(OH)CH_2O]_mH$ or

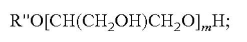

$R''O[CH(CH_2OH)CH_2O]_mH$;

in which formulae:

R" represents a saturated or unsaturated, linear or branched hydrocarbon-based radical comprising from 8 to 40 carbon atoms and preferably from 10 to 30 carbon atoms; m is an integer between 1 and 30, preferably between 1 and 10 and more particularly from 1.5 to 6; R" may optionally comprise heteroatoms, for instance oxygen and nitrogen. In particular, R" may optionally comprise one or more hydroxyl and/or ether and/or amide groups. R" preferably denotes mono- or polyhydroxylated $C_{10}$-$C_{20}$ alkyl, and/or alkenyl radicals.

Use may be made, for example, of the polyglycerolated (3.5 mol) hydroxylauryl ether sold under the name Chimexane® NF from Chimex.

The (poly)ethoxylated fatty alcohols that are suitable for performing the invention are chosen more particularly from alcohols containing from 8 to 30 carbon atoms, and preferably from 12 to 22 carbon atoms.

The (poly)ethoxylated fatty alcohols more particularly contain one or more linear or branched, saturated or unsaturated hydrocarbon-based groups, comprising 8 to 30 carbon atoms, which are optionally substituted, in particular with one or more (in particular 1 to 4) hydroxyl groups. If they are unsaturated, these compounds may comprise one to three conjugated or non-conjugated carbon-carbon double bonds.

The (poly)ethoxylated fatty alcohol(s) preferably have the following formula (XII):

(XII)

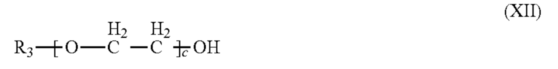

with $R_3$ representing a linear or branched $C_8$-$C_{40}$ alkyl or alkenyl group and preferably $C_8$-$C_{30}$ alkyl or alkenyl group, optionally substituted with one or more hydroxyl groups, and c is an integer between 1 and 200 inclusive, preferably between 2 and 50 and more particularly between 8 and 30, such as 20.

The (poly)ethoxylated fatty alcohols are more particularly fatty alcohols comprising from 8 to 22 carbon atoms, oxyethylenated with 1 to 30 mol of ethylene oxide (1 to 30 OE). Among these, mention may be made more particularly of lauryl alcohol 2 OE, lauryl alcohol 3 OE, decyl alcohol 3 OE, decyl alcohol 5 OE and oleyl alcohol 20 OE.

Mixtures of these (poly)oxyethylenated fatty alcohols may also be used.

Among the nonionic surfactants, use is preferably made of $C_6$-$C_{24}$ alkyl polyglucosides and (poly)ethoxylated fatty alcohols, $C_6$-$C_{16}$ alkyl polyglucosides are more particularly used.

According to an embodiment of the present invention, the at least one nonionic surfactant may be present in the composition according to the present invention in an amount from 0.2% to 20%, such as from 1% to 15%, or from 2% to 10%, relative to the total weight of the composition including all ranges and subranges therebetween. This embodiment can apply to various applications, including but not limited to shampoo products.

According to another embodiment of the present invention, the at least one nonionic surfactant may be present in the composition according to the present invention in an amount from 15% to 80%, such as from 20% to 70%, or from 25% to 50%, relative to the total weight of the composition including all ranges and subranges therebetween. This embodiment can apply to various applications, including but not limited to microemulsions, which are generally used as intermediates to formulate various cosmetic consumer goods.

Anionic Surfactant

According to an embodiment of the invention, the auxiliary component (B) may comprise at least one anionic surfactant.

The term "anionic surfactant" is understood to mean an amphiphilic compound with a hydrophobic part and a hydrophilic part wherein the hydrophilic part carries as ionic or ionisable group only anionic group with a cationic counterion which is generally metallic (alkali metal, such as Na or K) or ammonium, capable of dissociating to give anions in aqueous solution.

More particularly the anionic group of the anionic surfactant is belonging to the group chosen from: C(O)OH, $-C(O)O^-$, $-SO_3H$, $-S(O)_2O^-$, $-OS(O)_2OH$, $-OS(O)_2O^-$, $-P(O)OH_2$, $-P(O)_2O^-$, $-P(O)O_2^-$, $-P(OH)_2$, $=P(O)OH$, $-P(OH)O^-$, $=P(O)O^-$, $=POH$, $=PO^-$, the cationic counter anion being usually selected from alkali metal such as sodium, or alkaline earth metal such as magnesium, or organic cationic counter anion such as ammonium salts, amine salts, or aminoalcohol salts. The surfactants may also occur in their acid forms.

Mention may be made, as anionic surfactants, of surfactants comprising carboxylate, sulfate, sulfonate, sulfoacetate, sulfosuccinate, phosphate, isethionate, sarcosinate, glutamate, lactylate or taurate anionic groups, salts of fatty acids, salts of galactosiduronic acids, salts of ether carboxylic acids surfactants and their mixtures.

More particularly, the anionic surfactant according to the invention is chosen from:

- $(C_6\text{-}C_{30})$alkyl sulfates, $(C_6\text{-}C_{30})$alkyl ether sulfates, $(C_6\text{-}C_{30})$alkylamido ether sulfates, alkylaryl polyether sulfates or monoglyceride sulfates; preferably for this type of anionic surfactants, $(C_6\text{-}C_{30})$alkyl ether sulfates, alkylaryl polyether sulfates, or a mixture is used. Mentions may be made of sulfate of ether of lauryl alcohol and alkylene oxide, containing from 1 to 50 alkylene oxide groups.

More preferably, the anionic surfactant is chosen from sulfate of ether of lauryl alcohol and alkylene oxide containing from 1 to 4 alkylene oxide groups, especially ethylene oxide groups. For example, sodium laureth sulfate containing in average 2.2 ethylene oxide groups that are sold by the company Cognis (BASF) under the name Texapon® AOS 225 UP, Rhodia under the name Rhodapex® esb-70/fla3, Clariant under the name Genapol® LRO L'O, and sodium laureth sulfate containing in average 1 ethylene oxide group that is sold by the company Zhejiang Zanyu Technology under the name SLES (N1EO).

- $(C_6\text{-}C_{30})$alkyl sulfonates, $(C_6\text{-}C_{30})$alkylamidesulfonates, $(C_6\text{-}C_{30})$alkylaryl sulfonates, $\alpha$-olefin sulfonates, paraffin sulfonates;
- $(C_6\text{-}C_{30})$alkyl phosphates;
- $(C_6\text{-}C_{30})$alkyl sulfosuccinates, $(C_6\text{-}C_{30})$alkyl ether sulfosuccinates or $(C_6\text{-}C_{30})$alkylamido sulfosuccinates;
- $(C_6\text{-}C_{30})$alkyl sulfoacetates;
- $(C_6\text{-}C_{24})$acylsarcosinates;
- $(C_6\text{-}C_{24})$acylglutamates;
- $(C_6\text{-}C_{30})$alkylpolyglycoside carboxylic ethers;
- $(C_6\text{-}C_{30})$alkylpolyglycoside sulfosuccinates;
- $(C_6\text{-}C_{30})$alkyl sulfosuccinamates;
- $(C_6\text{-}C_{24})$acyl isethionates, for example sodium lauroyl methyl isethionate, sodium cocoyl isothionate; mentions may be made of the sodium lauroyl methyl isethionate which is sold under the trade name ISELUX® LQ-CLR-SB by the company Innospec Active Chemicals;
- N—$[(C_6\text{-}C_{24})$acyl] taurates;
- salts of fatty acids;
- $(C_8\text{-}C_{20})$acyl lactylates;
- salts of $(C_6\text{-}C_{30})$alkyl-D-galactosiduronic acids;
- salts of $(C_6\text{-}C_{30})$alkyl polyoxyalkylenated ether carboxylic acids, of $(C_6\text{-}C_{30})$alkylaryl polyoxyalkylenated ether carboxylic acids or of $(C_6\text{-}C_{30})$alkylamido polyoxyalkylenated ether carboxylic acids;
- and their mixtures.

The alkyl or acyl radicals of these various anionic surfactants preferably comprise from 12 to 20 carbon atoms.

Furthermore, the oxyalkylenated or polyoxyalkylenated anionic surfactants preferably comprise from 1 to 50 alkylene oxide groups, more preferably from 1 to 4 alkylene oxide groups, in particular ethylene oxide groups.

Advantageously, according to an embodiment, the present invention comprises at least one anionic surfactant chosen from $(C_6\text{-}C_{30})$alkyl sulfates, $(C_6\text{-}C_{30})$alkyl ether sulfates, $(C_6\text{-}C_{30})$alkylamido ether sulfates, alkylaryl polyether sulfates, monoglyceride sulfates, $(C_6\text{-}C_{24})$acyl isethionates, or a mixture thereof.

According to an embodiment of the present invention, the anionic surfactant is preferably chosen from sodium laureth sulfate, sodium lauroyl methyl isethionate, sodium cocoyl isethionate, or a mixture thereof.

According to an embodiment of the present invention, the anionic surfactant is sodium laureth sulfate containing in average 2.2 ethylene oxide groups.

According to an especially exemplary embodiment of the present invention, the composition may be free of any sulfate to be used as the anionic surfactant.

The at least one anionic surfactant may be present in the composition according to the present invention in an amount from 1% to 35%, such as from 5% to 20%, or from 8% to 15%, relative to the total weight of the composition including all ranges and subranges therebetween.

Amphoteric Surfactant

According to an embodiment of the invention, the auxiliary component (B) may comprise at least one amphoteric surfactant, which may also be called as zwitterionic surfactant.

The amphoteric or zwitterionic surfactant(s) that may be used in the present invention may be quaternized secondary or tertiary aliphatic amine derivatives containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of $(C_8\text{-}C_{20})$alkylbetaines, sulfobetaines, $(C_8\text{-}C_{20}$ alkyl)amido$(C_2\text{-}C_8$ alkyl) betaines and $(C_8\text{-}C_{20}$ alkyl)amido$(C_2\text{-}C_8$ alkyl)sulfobetaines.

Among the $(C_8\text{-}C_{20})$alkylbetaines, mentions may be made of behenylbetaine, cetyl betaine, cocoylbetaine, decylbetaine. From alkylbetaines, cocoylbetaine is preferred, for example the products sold by the company Rhodia under the tradename Mirataine® BB/FLA.

Among the optionally quaternized secondary or tertiary aliphatic amine derivatives that may be used, mention may also be made of the products of respective structures (A1) and (A2) below:

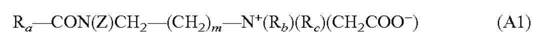

$$R_a—CON(Z)CH_2—(CH_2)_m—N^+(R_b)(R_c)(CH_2COO^-) \quad (A1)$$

in which:

- $R_a$ represents a $C_{10}\text{-}C_{30}$ alkyl or alkenyl group derived from an acid $R_a$—COOH preferably present in hydrolysed coconut oil, a heptyl group, a nonyl group or an undecyl group,
- $R_b$ represents a $\beta$-hydroxyethyl group,
- $R_c$ represents a carboxymethyl group;
- m is equal to 0, 1 or 2,
- Z represents a hydrogen atom or a hydroxyethyl or carboxymethyl group;

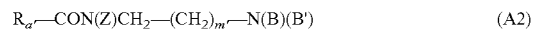

$$R_{a'}—CON(Z)CH_2—(CH_2)_{m'}—N(B)(B') \quad (A2)$$

in which:

- B represents $—CH_2CH_2OX'$, with X' representing $—CH_2—COOH$, $CH_2—COOZ'$, $—CH_2CH_2—COOH$, $—CH_2CH_2—COOZ'$, or a hydrogen atom,
- B' represents $—(CH_2)_z—Y'$, with z=1 or 2, and Y' representing $—COOH$, $—COOZ'$, $—CH_2—CHOH—SO_3H$ or $—CH_2—CHOH—SO_3Z'$, m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, $R_{a'}$ represents a $C_{10}$-$C_{30}$ alkyl or alkenyl group of an acid $R_{a'}COOH$ preferably present in hydrolysed linseed oil or coconut oil, an alkyl group, in particular a $C_{17}$ alkyl group, and its iso form, or an unsaturated $C_{17}$ group.

The compounds corresponding to formula (A1) may be preferred.

Among the compounds corresponding to formula (A1), mentions may be made of cocamidopropyl betaine, for example the product sold under the tradename Dehyton PK 45 by Cognis (BASF).

Use may also be made of the compounds of formula (A3):

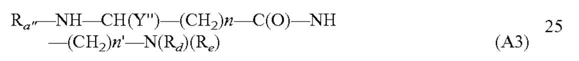

$R_{a''}$—NH—CH(Y")—$(CH_2)n$—C(O)—NH—$(CH_2)n'$—$N(R_d)(R_e)$ (A3)

in which:

$R_{a''}$ represents a $C_{10}$-$C_{30}$ alkyl or alkenyl group of an acid $R_{a''}$—C(O)OH preferably present in hydrolysed linseed oil or coconut oil;

Y" represents the group —C(O)OH, —C(O)OZ", —$CH_2$—CH(OH)—$SO_3H$ or the group —$CH_2$—CH(OH)—$SO_3$—Z", with Z" representing a cationic counterion resulting from an alkali metal or alkaline-earth metal, such as sodium, an ammonium ion or an ion resulting from an organic amine;

$R_d$ and $R_e$ represent, independently of each other, a $C_1$-$C_4$ alkyl or hydroxyalkyl radical; and n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name Chimexane HB.

Preferably, the amphoteric surfactants may be chosen from $(C_8$-$C_{20})$alkylbetaines, $(C_8$-$C_{20})$alkylamido$(C_1$-$C_6)$alkylbetaines, and mixtures thereof.

More preferably, the amphoteric or zwitterionic surfactant may be chosen from cocamidopropyl betaine, cocoylbetaine, or a mixture thereof.

The at least one amphoteric surfactant may be present in the composition according to the present invention in an amount from 1% to 20%, such as from 2% to 15%, or from 3% to 10%, relative to the total weight of the composition including all ranges and subranges therebetween.

According to an embodiment of the present invention, the surfactant comprises preferably a combination of anionic surfactant and amphoteric surfactant. More preferably, the surfactant of the invention contains a combination of a sulfate anionic surfactant and a betaine surfactant, such as a combination of sodium laureth sulfate and cocoylamidopropylbetaine. Without being restricted to any known theory, it is believed that such a combination can particularly benefit the cleansing ability of the shampoo, especially when the fatty acid-ester mixture (A) is incorporated for the anti-itching effect.

Cationic Surfactant

According to an embodiment of the invention, the auxiliary component (B) may comprise at least one cationic surfactant. Mention may be made, for example, of optionally polyoxyalkylenated primary, secondary or tertiary fatty amine salts, quaternary ammonium salts, and mixtures thereof.

Examples of quaternary ammonium salts that may especially be mentioned include:

a) those corresponding to the general formula (V) below:

(V)

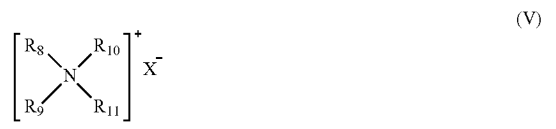

in which formula (V) the groups $R_8$ to $R_{11}$, which may be identical or different, represent a linear or branched aliphatic group comprising from 1 to 30 carbon atoms or an aromatic group such as aryl or alkylaryl, at least one of the groups $R_8$ to $R_{11}$ comprising from 8 to 30 carbon atoms and preferably from 12 to 24 carbon atoms. The aliphatic groups may comprise heteroatoms such as, in particular, oxygen, nitrogen, sulfur and halogens.

The aliphatic groups are chosen, for example, from $C_1$-$C_{30}$ alkyl, $C_1$-$C_{30}$ alkoxy, polyoxy$(C_2$-$C_6)$alkylene, $C_1$-$C_{30}$ alkylamide, $(C_{12}$-$C_{22})$alkylamido$(C_2$-$C_6)$alkyl, $(C_{12}$-$C_{22})$alkylacetate, $C_1$-$C_{30}$ hydroxyalkyl, $X^-$ is an anionic counterion chosen from halides, phosphates, acetates, lactates, $(C_1$-$C_4)$alkyl sulfates, and $(C_1$-$C_4)$alkyl- or $(C_1$-$C_4)$alkylarylsulfonates.

Among the quaternary ammonium salts of formula (V), preference is given firstly to tetraalkylammonium halides such as tetraalkylammonium chlorides, for instance tetraalkylammonium or alkyltrimethylammonium halides such as dialkyldimethylammonium or alkyltrimethylammonium chlorides in which the alkyl group contains from approximately 12 to 22 carbon atoms, in particular halides such as behenyltrimethylammonium chloride, distearyldimethylammonium chloride, cetyltrimethylammonium chloride, benzyldimethylstearylammonium chloride, or else, secondly, alkoxy sulfates, especially distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium halide, particularly the chloride or stearamidopropyldimethyl(myristyl acetate)ammonium chloride, sold under the name Ceraphyl® 70 by the company Van Dyk;

b) quaternary ammonium salts of imidazoline, for instance those of formula (VI) below:

(VI)

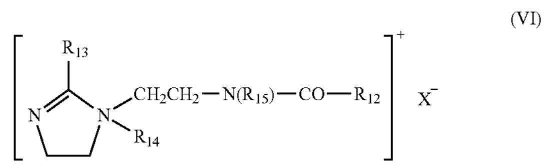

in which formula (VI):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an anionic counterion chosen in particular from halides, phosphates, acetates, lactates, ($C_1$-$C_4$) alkyl sulfates, ($C_1$-$C_4$)alkyl- or ($C_1$-$C_4$)alkylarylsulfonates.

$R_{12}$ and $R_{13}$ preferably denote a mixture of alkyl or alkenyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

c) quaternary diammonium or triammonium salts, particularly of formula (VII) below:

(VII)

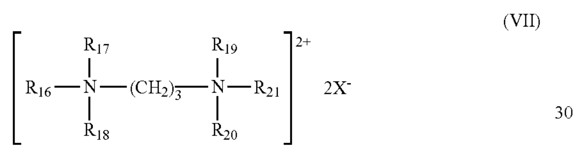

in which formula (VII):

$R_{16}$ denotes an alkyl group comprising from about 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group $—(CH_2)_3—N^+(R_{16a})(R_{17a})(R_{18a})$; $R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms, and $X^-$ represents an anionic counterion chosen in particular from halides, acetates, phosphates, nitrates, ($C_1$-$C_4$) alkyl sulfates, ($C_1$-$C_4$)alkyl- or ($C_1$-$C_4$)alkylarylsulfonates, in particular methyl sulfate and ethyl sulfate. Such compounds are, for example, Finquat CT-P, available from the company Finetex (Quaternium 89), and Finquat CT, available from the company Finetex (Quaternium 75);

d) quaternary ammonium salts containing one or more ester functions, such as those of formula (VIII) below:

(VIII)

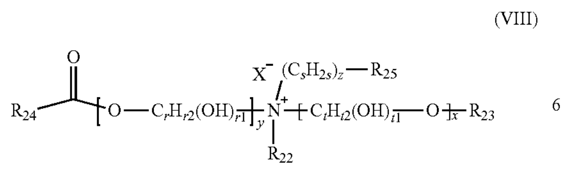

in which formula (VIII):

$R_{22}$ is chosen from $C_1$-$C_6$ alkyl and $C_1$-$C_6$ hydroxyalkyl or dihydroxyalkyl groups;

$R_{23}$ is chosen from:

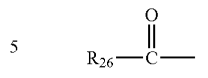

the group linear or branched, saturated or unsaturated $C_1$-$C_{22}$ hydrocarbon-based groups $R_{27}$, a hydrogen atom;

$R_{25}$ is chosen from:

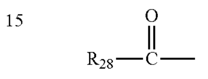

the group linear or branched, saturated or unsaturated $C_1$-$C_6$ hydrocarbon-based groups $R_{29}$, a hydrogen atom;

$R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6;

r1 and t1, which may be identical or different, are equal to 0 or 1, with r2+r1=2r and t1+t2=2t, y is an integer ranging from 1 to 10;

x and z, which may be identical or different, are integers ranging from 0 to 10;

$X^-$ represents an organic or inorganic anionic counterion;

with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and may contain from 12 to 22 carbon atoms, or may be short and may contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion $X^-$ is preferably a halide, preferably such as chloride, bromide or iodide, a ($C_1$-$C_4$)alkyl sulfate or a ($C_1$-$C_4$)alkyl- or ($C_1$-$C_4$)alkylaryl-sulfonate. However, use may be made of methanesulfonate, phosphate, nitrate, tosylate, an anion derived from an organic acid, such as acetate or lactate, or any other anion compatible with the ammonium containing an ester function.

The anionic counterion $X^-$ is even more particularly chloride, methyl sulfate or ethyl sulfate.

Use is made more particularly, in the composition according to the invention, of the ammonium salts of formula (VIII) in which:

$R_{22}$ denotes a methyl or ethyl group, x and y are equal to 1, z is equal to 0 or 1, r, s and t are equal to 2, $R_{23}$ is chosen from:

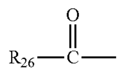

the group methyl, ethyl or C14-C22 hydrocarbon-based groups, a hydrogen atom, $R_{25}$ is chosen from:

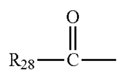

the group a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and more particularly from linear or branched, saturated or unsaturated $C_{13}$-$C_{17}$ alkyl and alkenyl groups.

Advantageously, the hydrocarbon-based radicals are linear.

Among the quaternary ammonium salts containing one or more ester functions of formula (VIII), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably methyl or ethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of mono-, di- and triesters with a weight majority of diester salts.

It is also possible to use the ammonium salts containing at least one ester function that are described in U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethyl ammonium methosulfate, and mixtures thereof.

Advantageously, the content of at least one cationic surfactant represents from 4% to 50% by weight, with respect to the weight of the composition, preferably from 6% to 40% by weight, more preferably from 10% to 20% by weight, even more preferably from 12% to 16% by weight with respect to the weight of the composition.

Cationic Polymers

According to a preferred embodiment, the auxiliary component (B) of the present invention may further comprise at least one cationic polymer.

The term "cationic polymer" means any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5\times10^6$ approximately and preferably between $10^3$ and $3\times10^6$ approximately.

There is no limitation on the types of cationic polymers that are suitable for the present invention. Mentions may be made of homopolymers or copolymers derived from acrylic or methacrylic esters or amides, cationic polysaccharides, polymers formed from piperazinyl units and divalent alkylene or hydroxyalkylene radicals containing straight or branched chains, water-soluble polyamino amides prepared in particular by polycondensation of an acidic compound with a polyamine, polyamino amide derivatives resulting from the condensation of polyalkylene polyamines with polycarboxylic acids followed by alkylation with bifunctional agents, polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms, cyclopolymers of alkyldiallylamine or of dialkyldiallylammonium, quaternary diammonium polymers, polyquaternary ammonium polymers, quaternary polymers of vinylpyrrolidone and of vinylimidazole, polyamines, homopolymers or copolymers comprising one or more units derived from vinylamine and optionally one or more units derived from vinylformamide, or a mixture thereof.

Preferably, the composition of the present invention may further comprise, as a cationic polymer, at least one cationic polysaccharide.

Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are especially described in French patent 1 492 597, and mention may be made of the polymers sold under the name UCARE POLYMER "JR" (JR 400 LT, JR 125 and JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group. Cationic cellulose copolymers or cellulose derivatives grafted with a water-soluble quaternary ammonium monomer are described especially in U.S. Pat. No. 4,131,576, and mention may be made of hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names CELQUAT L 200 and CELQUAT H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, chloride). Such products are especially sold under the names JAGUAR C13 S, JAGUAR C 15, JAGUAR C 17 or JAGUAR C162 by the company Rhodia (INCI: hydroxypropyl guar hydroxypropyltrimonium chloride).

When exists, the cationic polymer is present in an amount ranging from 0.001% to 10% by weight, preferably from 0.005% to 5% by weight, more preferably from 0.01% to 3% by weight, relative to the total weight of the composition.

Additional Additives

According to various embodiments, the compositions of the present invention are provided for application to keratin materials, such as skin, scalp or hair. In accordance with these embodiments, the compositions of the present invention can comprise, e.g., in component (B), ingredients conventionally useful in compositions for caring for keratin materials, such as, active ingredients, humectants, additional fatty substances, antidandruff agents, anti-seborrhoea agents, agents for preventing hair loss and/or for promoting hair regrowth, vitamins and provitamins including panthenol, sunscreens, sequestrants, plasticizers, solubilizers, acidifying agents, opacifiers, pearlescent or nacreous agents, antioxidants, hydroxyacids, fragrances and preserving agents.

A non-exhaustive listing of such ingredients can be found in U.S. patent application publication no. 2004/0170586, the entire contents of which is hereby incorporated by reference. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These additives may be selected variously by the person skilled in the art in order to prepare a composition which has the desired properties, for example, consistency or texture. In particular, the additives, if used, and the amounts thereof are particularly determined according to the specific products/applications thereof, e.g., lotion, leave-on conditioner, shampoo, cream, rinse-off conditioner, emulsion/microemulsion and the like.

These additives may be present in the composition in a proportion from 0.01% to 90% relative to the total weight of the composition and further such as from 0.1% to 50% (if present), including all ranges and subranges therebetween.

Method and Use

The composition according to the present invention can be generally prepared according to the general knowledge of a person skilled in the art. Nevertheless, it is to be understood that a person skilled in the art can choose the method of preparation, on the basis of his/her general knowledge, taking into account the nature of the constituents used, for example, their solubility in the vehicle, and the application envisaged for the compositions or the kit.

According to an embodiment, the composition according to the present invention can be used for caring for keratin materials, especially the skin, scalp and/or hair. This use may manifest itself as a process for caring for keratin materials, especially the skin, scalp and/or hair, comprising the step applying to said keratin materials the composition of the invention.

The composition according to the present invention can be provided in various forms, e.g., as consumer goods directly or as intermediates to formulate consumer goods. For example, an anionic surfactant can be comprised in the composition to provide a shampoo product. For another example, a cationic surfactant can be comprised in the composition to provide a conditioner product, for conditioning hair, skin, scalp and the like. For still another example, a nonionic surfactant can be comprised, in a relatively high amount, in the composition to provide a microemulsion, which is in turn used to formulate various consumer goods, e.g., shampoo, especially a transparent shampoo.

The various forms of the compositions can be prepared according to methods conventionally known in the art, as long as the fatty acid-ester mixture (A) according to the present invention can be introduced in an anti-itching effective amount into the desired form.

The invention will be further illustrated by the following examples, which set forth particularly advantageous embodiments.

Notwithstanding that the numerical ranges and parameters setting forth the broad scope of the present invention are approximations, the numerical values set forth in the specific examples are reported as precisely as possible. Any numerical value, however, inherently contain certain errors necessarily resulting from the standard deviation found in their respective measurements. The following examples are intended to illustrate the present invention without limiting the scope as a result.

EXAMPLES

The ingredient amounts/concentrations in the compositions/formulas described below were expressed in % by weight, relative to the total weight of each composition/formula.

Material:

*COCOS NUCIFERA* (COCONUT) OIL: activated virgin coconut oil (AVCO), available from BIOTROPICS Other materials without specification here were each commercially available.

Example 1

Compositions A, and comparative compositions A' and A", as Table 1 were formulated:

TABLE 1

| Sulfate free shampoo A and comparative A' and A" | | | |
|---|---|---|---|
| | A | A' | A" |
| SODIUM LAUROYL SARCOSINATE (SP CRODASINIC LS30SNT MBAL-LQ-(RB) from CRODA) | 6 | 6 | 6 |
| SODIUM COCOYL ISETHIONATE (HOSTAPON SCI 85 C from CLARIANT) | 3.4 | 3.4 | 3.4 |
| COCO-BETAINE (AMPHITOL 24B-2 from KAO) | 4 | 4 | 4 |
| LAURIC ACID (CREMERAC C 12/99-LAURIC ACID from PETER CREMER) | 0.7 | 0.7 | 0.7 |
| SALICYLIC ACID | 0.2 | 0.2 | 0.2 |
| SODIUM BENZOATE | 0.5 | 0.5 | 0.5 |
| HYDROXYPROPYL GUAR HYDROXYPROPYLTRI-MONIUM CHLORIDE (JAGUAR C 162 SGI from RHODIA (SOLVAY)) | 0.25 | 0.25 | 0.25 |
| HYDROXYPROPYL GUAR (JAGUAR HP 105 SGI from RHODIA (SOLVAY)) | 0.3 | 0.3 | 0.3 |
| *COCOS NUCIFERA* (COCONUT) OIL - activated virgin coconut oil of the invention | 0.9 | — | 0 |
| *COCOS NUCIFERA* (COCONUT) OIL virgin coconut, oil without activation (AGRIPURE AP-20 from CARGILL) | 0 | 0 | 0.9 |
| CITRIC ACID | 0.2 | 0.2 | 0.2 |
| WATER | QS to 100 | QS to 100 | QS to 100 |

The above listed compositions A, A' and A" were prepared according to known manufacturing method of field.

Compositions A and A' and A" were obtained in shampoo product according to the present invention.

Compositions B as Table 2 was formulated:

TABLE 2

| Shampoo B | |
|---|---|
| INCI US | B |
| WATER | QS to 100 |
| SODIUM LAURETH SULFATE (AE2S-70 from LIANSHUI XINYUAN BIOLOGY) | 14 |
| COCO-BETAINE | 2.6 |
| SALICYLIC ACID | 0.2 |
| SODIUM BENZOATE | 0.5 |
| GUAR HYDROXYPROPYL-TRIMONIUM CHLORIDE (CATCOL C 135 (L) from LUCID COLLOIDS) | 0.2 |
| CARBOMER (ACRYPOL 980 from COREL PHARMA CHEM) | 0.4 |

TABLE 2-continued

| Shampoo B | |
|---|---|
| INCI US | B |
| *COCOS NUCIFERA* (COCONUT) OIL | 0.9 |
| OCTYLDODECANOL (EUTANOL G from BASF) | 0.5 |

The above listed composition B was prepared according to known manufacturing method of field.

Composition C as Table 3 was formulated:

TABLE 3

| Lotion for scalp | |
|---|---|
| INCI US | C |
| WATER | QS to 100 |
| BEHENTRIMONIUM CHLORIDE | 0.22 |
| QUATERNIUM-87 | 0.3 |
| POLYSORBATE 20 | 0.3 |
| STEARYL ALCOHOL | 0.2 |
| CHLORHEXIDINE DIGLUCONATE | 0.2 |
| POLYQUATERNIUM-37 | 0.5 |
| *COCOS NUCIFERA* (COCONUT) OIL | 0.3 |
| FRAGRANCE | 0.5 |

The above listed composition C was prepared according to known manufacturing method of field.

Composition D as Table 4 was formulated:

TABLE 4

| INCI US | D |
|---|---|
| WATER | QS to 100 |
| BRASSICAMIDOPROPYL DIMETHYLAMINE | 1.5 |
| GLYCERYL STEARATE | 0.5 |
| CETEARYL ALCOHOL | 7 |
| CETYL ESTERS | 1.5 |
| CAPRYLYL GLYCOL | 0.3 |
| *COCOS NUCIFERA* (COCONUT) OIL | 0.9 |
| TARTARIC ACID | 0.3 |

The above listed composition D was prepared according to known manufacturing method of field.

Example 2

The soothing feeling of the composition A was evaluated. 5 volunteers between age of 25 and 45 applied the composition A on the hair and scalp every day for 3 weeks, followed by 2 weeks without using the Composition A. The anti-itchy feeling (soothing feeling) was assessed in the total 5 weeks. Scores of itchy feeling before the application of the Composition A was given as a baseline, the scores of itchy feeling after application of the Composition A was given every day, the mean difference was shown in the FIG. 1.

Scores were given and calculated as follows:

In the first 3 weeks, each volunteer washed hair with the composition A at every evening, in which the conventional usage of each volunteer was used. In the next 2 weeks, each volunteer washed hair with a standard shampoo without AVCO also at every evening, in which the conventional usage of each volunteer was still used.

Volunteers gave scores to the itching feeling, where:

0 meant unchanged;

−1 meant fairly improved;

−2 meant significantly improved; and

−3 meant substantially free of itching feeling.

The average scores of the 5 volunteers were counted and plotted in FIG. 1.

Referring to FIG. 1, less the score, less the itchy feeling was. It was observed that the Composition A showed a very good and long term anti-itchy feeling, even 2 weeks after the last application of the Composition A.

Example 3

The suppleness effect on the hair were evaluated using the composition A and comparative composition A". Hair swatches were washed using the compositions A and A" respectively, then dried out. The hair swatches were subsequently tested by instrument HYACINTHE CN from AJ AUTOMATION for bending test. The result was shown in FIG. 2.

Figure 2:
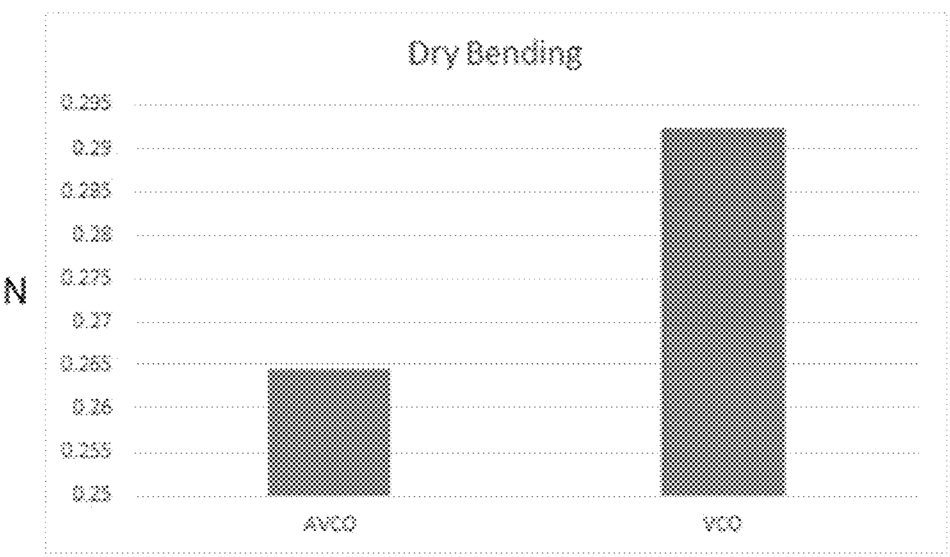

Referring to FIG. 2, it was observed that compared with conventional shampoo without using AVCO, e.g., even having VCO which comprised medium chain fatty acids without esterification thereof, the dry bending performance of composition A was significantly better.

The invention claimed is:

1. A composition for caring for keratin materials, comprising:

(A) a fatty acid-ester mixture comprising:

(A-I) a fatty acid component comprising at least 3 medium chain fatty acids, comprising:

caprylic acid in an amount of 5-20 wt %;

capric acid in an amount of 1-10 wt %; and lauric acid in an amount of 20-70 wt %, and (A-II) the corresponding monoglycerides of each of the at least 3 medium chain fatty acids in component (A-I), comprising:

monocaprylin in an amount of 0.5-15 wt %;

monocaprin in an amount of 0.1-10 wt %; and monolaurin in an amount of 10-40 wt %, each relative to the total amount of the fatty acid component (A-I) and the corresponding monoglycerides (A-II);

(B) a cosmetically or dermatologically acceptable auxiliary agent to assist the delivery of the fatty acid-ester mixture (A) to the keratin materials;

(C) a combination of (1) an anionic surfactant selected from the group consisting of ($C_6$-$C_{24}$) acyl isethionates, ($C_6$-$C_{24}$) acyl sarcosinates and mixtures thereof with (2) a betaine surfactant, (D) a cationic polymer comprising a homopolymer or copolymer derived from acrylic or methacrylic esters or amides, and/or a cationic galactomannan gum, and (E) water, wherein the fatty acid-ester mixture (A) is present in the composition in an amount ranging from 0.3% to 1.5% by weight, relative to the total weight of the composition, a total amount of the fatty acids of component (A-I) and a total amount of the corresponding monoglycerides (A-II) are present in a ratio ranging from 2.5:1 to 1.5:1, the anionic surfactant is present in the composition in an amount from 8% to 15% by weight, relative to the total weight of the composition, the betaine surfactant is present in the composition in an amount from 1% to 10% by weight, relative to the total weight of the composition, the cationic polymer is present in the composition in an amount from 0.01% to 3% by weight, relative to the total weight of the composition, and the water is present in the composition in an amount of 15% by weight or more, relative to the total weight of the composition.

2. The composition according to claim 1, wherein the fatty acid component (A-I) further comprises at least one medium chain fatty acid selected from the group consisting of myristic acid, palmitic acid, stearic acid, and arachidic acid; while the corresponding monoglycerides (A-II) further comprise a monoglyceride of each of the at least one medium chain fatty acid.

3. The composition according to claim 1, wherein a multiester formed from the at least 3 medium chain fatty acids of the fatty acid component (A-I) and glycerol, is comprised in the fatty acid-ester mixture (A).

4. The composition according to claim 3, wherein the multiester includes a diester or a triester.

5. The composition according to claim 1, wherein the fatty acid-ester mixture (A) is activated virgin coco oil comprising:

as the fatty acid component (A-I):

caprylic acid in an amount of 8-10 wt %;

capric acid in an amount of 4-7 wt %; and lauric acid in an amount of 40-55 wt %;

and as the corresponding monoglycerides (A-II):

monocaprylin in an amount of 4-7 wt %;

monocaprin in an amount of 3-5 wt %; and monolaurin in an amount of 20-30 wt %;

each relative to the total amount of the fatty acid component (A-I) and the corresponding monoglycerides (A-II).

6. The composition according to claim 5, wherein the activated virgin coco oil comprises:

the fatty acid component (A-I) in an amount of 5-40 wt %;

the corresponding monoglycerides (A-II) in an amount of 1-30 wt %;

diglycerides of caprylic acid, capric acid, and lauric acid, in a total amount of 10-50 wt %; and triglycerides of caprylic acid, capric acid, and lauric acid, in a total amount of 10-70 wt %;

each relative to the total amount of the activated virgin coco oil.

7. The composition according to claim 5, wherein the activated virgin coco oil comprises:

the fatty acid component (A-I) in an amount of 20-25 wt %;

the corresponding monoglycerides (A-II) in an amount of 10-15 wt %;

diglycerides of caprylic acid, capric acid, and lauric acid, in a total amount of 30-40 wt %; and triglycerides of caprylic acid, capric acid, and lauric acid, in a total amount of 20-30 wt %;

each relative to the total amount of the activated virgin coco oil.

8. The composition according to claim 1, wherein the cosmetically or dermatologically acceptable auxiliary agent (B) comprises an organic solvent, and optionally a cationic surfactant.

9. A non-therapeutic method for soothing the itching feeling of keratin materials, comprising applying the composition of claim 1 to the keratin materials.

* * * * *